United States Patent [19]

Hoffman

[11] Patent Number: 5,747,079
[45] Date of Patent: May 5, 1998

[54] OXYGENATED BEVERAGE

[76] Inventor: Howard L. Hoffman, 3402 Waverley St., Palo Alto, Calif. 94306

[21] Appl. No.: 766,155

[22] Filed: Dec. 12, 1996

[51] Int. Cl.$^6$ ........................................ A23L 2/26
[52] U.S. Cl. .................. 426/67; 426/324; 426/330; 426/477; 426/590; 424/52
[58] Field of Search ................. 424/52; 426/67, 426/324, 330, 477, 590

[56] References Cited

U.S. PATENT DOCUMENTS 3,728,129  4/1973  Sargeant.
4,027,045  5/1977  Fedotkin et al..
4,689,215  8/1987  Ratcliff.
5,006,352  4/1991  Zelenák née Zoltai et al..

FOREIGN PATENT DOCUMENTS

WO 95/01774  1/1995  WIPO.
WO 95/27472  10/1995  WIPO.

*Primary Examiner*—Keith MacMillan
*Attorney, Agent, or Firm*—Townsend and Townsend and Crew, LLP

[57] ABSTRACT

The invention provides oxygenated solutions, such as beverages, useful for the alleviation of halitosis. Further provided are methods of using these solutions in remediating mouth odor.

5 Claims, No Drawings

OXYGENATED BEVERAGE

FIELD OF THE INVENTION

This invention is generally directed to compositions and their methods of use as a beverage, beneficial to oral hygiene, and more specifically, for the remediation of halitosis and to methods of using an oxygenated beverage as part of a regimen to reduce, control or eliminate halitosis.

BACKGROUND OF THE INVENTION

Malador of the oral cavity, also known as halitosis or bad breath, is an undesirable condition for many people. It is generally believed that a significant cause of such malador is the presence of anaerobic bacteria at the back of the tongue. The bacteria generate volatile sulfur compounds by degrading sulfur containing amino acids present in the mouth, and the exhalation of the volatile sulfur compounds is perceived as bad breath.

The volatile sulfur compounds, primarily hydrogen sulfide, methyl mercaptan, and dimethyl mercaptan, are recognized in the current dental literature as being major contributors to oral malador. In most persons, hydrogen sulfide and methylmercaptan constitute over 90% of the total volatile sulfur content identified in mouth air. These maladorous sulfur compounds are generated primarily through the putrefactive action of oral microorganisms on sulfur containing amino acids, peptones or proteins found in the mouth. These substrates are readily available in saliva and dental plaque or may be derived from proteinaceous food particles trapped between the teeth, in the gingival crevice or adhering to the mucous membranes and the irregular surface of the tongue. People with periodontal disease also have an attendant increase in malador due to disintegrated epithelial cells in periodontal pockets.

The prior art has attempted to treat halitosis by methods wherein the oral cavity is rinsed with an aqueous solution of stabilized chlorine dioxide. Examples include U.S. Pat. Nos. 5,200,171, and 4,689,215 issued to Perry A. Ratcliff and PCT Publication No. WO 95/27472.

There are scientific and medically based concerns over the byproducts formed when organics present in water are oxidized by chlorine dioxide. Partly for this reason, the United States Environmental Protection Agency currently limits the use of chlorine dioxide to the order of 0.002% for disinfecting drinking water. Oral rinses containing chlorine dioxide, in the range of 0.005%–0.5% have been shown to be effective in the control of halitosis; however, these concentrations are in excess of the accepted levels in drinking water. Thus, while effective against halitosis, oral rinses containing chlorine dioxide are generally not desirable for ingestion.

Concentrations of carbon dioxide in excess of the saturation concentration occur in many beverages as the result of natural processes. Beer, sparkling wine, and spring water are examples of beverages which develop supersaturated concentrations of carbon dioxide.

Concentrations of oxygen in excess of the saturation concentration do not occur in beverages, including water, as the result of natural processes.

The mouth is known to contain numerous species of bacteria. Bacteria which utilize matter for synthesis in the absence of oxygen are known as anaerobes, or anaerobic bacteria. Bacteria which utilize matter for synthesis in the presence of oxygen are known as aerobes, or aerobic bacteria. The bacteria which produce volatile sulfur compounds in the mouth are anaerobes.

Any beverage which is consumed that contains high concentrations of oxygen will tend to favor the development of aerobic bacteria in the mouth. As a beverage is ingested, it will pass over the anterior dorsal surface of the tongue and come into contact with deeper portions of the oral cavity which are difficult to reach with an oral rinse.

An oral rinse must be either expectorated or ingested. Thus, if there is any concern about the impact of an oral rinse on the user, the oral rinse must be expectorated after use. Furthermore, the use of an oral rinse in public situations would call attention to oneself in a socially disadvantageous manner.

For an individual suffering from chronic halitosis or for an individual concerned about the possibility of halitosis, the ability to ingest a beverage tending to ameliorate halitosis is of great benefit in situations where an oral rinse would be undesirable. This invention fulfills this and related needs.

SUMMARY OF THE INVENTION

One aspect of this invention provides a method of alleviating a condition of halitosis in a person, the method comprising contacting the person's oral cavity with an aqueous solution containing an effective amount of a supersaturated concentration of dissolved oxygen. Preferably an aqueous beverage solution in which the oxygen is present at a concentration from about 20 to about 1000 mg/l is used. Contacting is conveniently effected by ingestion, gargling, spraying and the like, just as with any other beverage, and whenever the person feels is appropriate.

Another aspect of the invention provides a method of forming a sealed, pressurized aqueous solution containing a supersaturated concentration of dissolved oxygen, the method comprising:

(a) passing a stream of pressurized oxygen into an aqueous solution in a container until the dissolved oxygen concentration reaches a predetermined pressurized level above saturation; and (b) sealing the container to form the sealed, pressurized aqueous solution. Perferably, the method uses ozonized oxygen and the aqueous solution is a beverage.

DETAILED DESCRIPTION

This invention provides a method of alleviating a condition of halitosis in a person, the method comprising contacting the person's oral cavity, typically by ingesting an aqueous solution containing an effective amount of dissolved oxygen. The solution, typically a beverage, of this invention, will contain dissolved oxygen in an amount effective to reduce halitosis. These amounts will be concentrations sufficient to inhibit the anaerobic bacteria and stimulate the aerobic bacteria in the oral cavity of those individuals suffering from halitosis. Typically, dissolved oxygen will be present at a concentration of from about 20 to about 1000 mg/l, preferably about 40 to 400 mg/l.

The method of dissolving supersaturated concentrations of oxygen into a solution can apply to virtually any aqueous solution, such as a beverage. Water; mineral water; water with added flavoring agents such as mint, lemon, citrus oils, and sweeteners; tea; herbal teas; fruit juices; coffee; cola; root beer and mouthwash are examples of beverages with or without carbonation, which can be supersaturated with oxygen in order to produce the desired benefit of reducing halitosis caused by anaerobic bacteria in the oral cavity.

A problem arises in that oxygen in a beverage can support microbial growth within the beverage. If the beverage is consumed within a short time (on the order of an hour or less) of the addition of oxygen, there is little reason for concern about microbial growth. However, if a beverage is to be bottled with oxygen present, especially supersaturated concentrations of oxygen, then it is necessary that the beverage and the container be completely sterile (absent of any microbes, including bacteria, fungi, and algae).

The aqueous medium is generally prefiltered to remove bacteria, treated with an antibacterial agent, or can be heated for sterilization.

(a) passing a stream of pressurized ozonized oxygen into an aqueous solution in a container until the dissolved oxygen concentration reaches a predetermined pressurized level above saturation; and (b) sealing the container.

Supersaturated concentrations of dissolved oxygen are those above the maximum that will occur naturally given a specific water temperature and atmospheric pressure. Table 1 gives the saturated concentrations for dissolved over a range of temperatures and pressures.

TABLE 1

Dissolved-oxygen concentration in water as a function of temperature and barometric pressure (salinity = 0 ppt)*
Dissolved-oxygen concentration, mg/L
Barometric pressure, millimeters of mercury

| Temp. °C. | 735 | 740 | 745 | 750 | 755 | 760 | 765 | 770 | 775 | 780 |
|---|---|---|---|---|---|---|---|---|---|---|
| 0 | 14.12 | 14.22 | 14.31 | 14.41 | 14.51 | 14.60 | 14.70 | 14.80 | 14.89 | 14.99 |
| 1 | 13.73 | 13.82 | 13.92 | 14.01 | 14.10 | 14.20 | 14.29 | 14.39 | 14.48 | 14.57 |
| 2 | 13.36 | 13.45 | 13.54 | 13.63 | 13.72 | 13.81 | 13.90 | 14.00 | 14.09 | 14.18 |
| 3 | 13.00 | 13.09 | 13.18 | 13.27 | 13.36 | 13.45 | 13.53 | 13.62 | 13.71 | 13.80 |
| 4 | 12.66 | 12.75 | 12.83 | 12.92 | 13.01 | 13.09 | 13.18 | 13.27 | 13.35 | 13.44 |
| 5 | 12.33 | 12.42 | 12.50 | 12.59 | 12.67 | 12.76 | 12.84 | 12.93 | 13.01 | 13.10 |
| 6 | 12.02 | 12.11 | 12.19 | 12.27 | 12.35 | 12.44 | 12.52 | 12.60 | 12.68 | 12.77 |
| 7 | 11.72 | 11.80 | 11.89 | 11.97 | 12.05 | 12.13 | 12.21 | 12.29 | 12.37 | 12.45 |
| 8 | 11.44 | 11.52 | 11.60 | 11.67 | 11.75 | 11.83 | 11.91 | 11.99 | 12.07 | 12.15 |
| 9 | 11.16 | 11.24 | 11.32 | 11.40 | 11.47 | 11.55 | 11.63 | 11.70 | 11.78 | 11.86 |
| 10 | 10.90 | 10.98 | 11.05 | 11.13 | 11.20 | 11.28 | 11.35 | 11.43 | 11.50 | 11.58 |
| 11 | 10.65 | 10.72 | 10.80 | 10.87 | 10.94 | 11.02 | 11.09 | 11.16 | 11.24 | 11.31 |
| 12 | 10.41 | 10.48 | 10.55 | 10.62 | 10.69 | 10.77 | 10.84 | 10.91 | 10.98 | 11.05 |
| 13 | 10.17 | 10.24 | 10.31 | 10.38 | 10.46 | 10.53 | 10.60 | 10.67 | 10.74 | 10.81 |
| 14 | 9.95 | 10.02 | 10.09 | 10.16 | 10.23 | 10.29 | 10.36 | 10.43 | 10.50 | 10.57 |
| 15 | 9.73 | 9.80 | 9.87 | 9.94 | 10.00 | 10.07 | 10.14 | 10.21 | 10.27 | 10.34 |
| 16 | 9.53 | 9.59 | 9.66 | 9.73 | 9.79 | 9.86 | 9.92 | 9.99 | 10.06 | 10.12 |
| 17 | 9.33 | 9.39 | 9.46 | 9.52 | 9.59 | 9.65 | 9.72 | 9.78 | 9.85 | 9.91 |
| 18 | 9.14 | 9.20 | 9.26 | 9.33 | 9.39 | 9.45 | 9.52 | 9.58 | 9.64 | 9.71 |
| 19 | 8.95 | 9.01 | 9.07 | 9.14 | 9.20 | 9.26 | 9.32 | 9.39 | 9.45 | 9.51 |
| 20 | 8.77 | 8.83 | 8.89 | 8.95 | 9.02 | 9.08 | 9.14 | 9.20 | 9.26 | 9.32 |
| 21 | 8.60 | 8.66 | 8.72 | 8.78 | 8.84 | 8.90 | 8.96 | 9.02 | 9.08 | 9.14 |
| 22 | 8.43 | 8.49 | 8.55 | 8.61 | 8.67 | 8.73 | 8.79 | 8.84 | 8.90 | 8.96 |
| 23 | 8.27 | 8.33 | 8.39 | 8.44 | 8.50 | 8.56 | 8.62 | 8.68 | 8.73 | 8.79 |
| 24 | 8.11 | 8.17 | 8.23 | 8.29 | 8.34 | 8.40 | 8.46 | 8.51 | 8.57 | 8.63 |
| 25 | 7.96 | 8.02 | 8.08 | 8.13 | 8.19 | 8.24 | 8.30 | 8.36 | 8.41 | 8.47 |
| 26 | 7.82 | 7.87 | 7.93 | 7.98 | 8.04 | 8.09 | 8.15 | 8.20 | 8.26 | 8.31 |
| 27 | 7.68 | 7.73 | 7.79 | 7.84 | 7.89 | 7.95 | 8.00 | 8.06 | 8.11 | 8.17 |
| 28 | 7.54 | 7.59 | 7.65 | 7.70 | 7.75 | 7.81 | 7.86 | 7.91 | 7.97 | 8.02 |
| 29 | 7.41 | 7.46 | 7.51 | 7.57 | 7.62 | 7.67 | 7.72 | 7.78 | 7.83 | 7.88 |
| 30 | 7.28 | 7.33 | 7.38 | 7.44 | 7.49 | 7.54 | 7.59 | 7.64 | 7.69 | 7.75 |
| 31 | 7.16 | 7.21 | 7.26 | 7.31 | 7.36 | 7.41 | 7.46 | 7.51 | 7.46 | 7.62 |
| 32 | 7.04 | 7.09 | 7.14 | 7.19 | 7.24 | 7.29 | 7.34 | 7.39 | 7.44 | 7.49 |
| 33 | 6.92 | 6.97 | 7.02 | 7.07 | 7.12 | 7.17 | 7.22 | 7.27 | 7.31 | 7.36 |
| 34 | 6.80 | 6.85 | 6.90 | 6.95 | 7.00 | 7.05 | 7.10 | 7.15 | 7.20 | 7.24 |
| 35 | 6.69 | 6.74 | 6.79 | 6.84 | 6.89 | 6.93 | 6.98 | 7.03 | 7.08 | 7.13 |
| 36 | 6.59 | 6.63 | 6.68 | 6.73 | 6.78 | 6.82 | 6.87 | 6.92 | 6.97 | 7.01 |
| 37 | 6.48 | 6.53 | 6.57 | 6.62 | 6.67 | 6.72 | 6.76 | 6.81 | 6.86 | 6.90 |
| 38 | 6.38 | 6.43 | 6.47 | 6.52 | 6.56 | 6.61 | 6.66 | 6.70 | 6.75 | 6.80 |
| 39 | 6.28 | 6.33 | 6.37 | 6.42 | 6.46 | 6.51 | 6.56 | 6.60 | 6.65 | 6.69 |
| 40 | 6.18 | 6.23 | 6.27 | 6.32 | 6.36 | 6.41 | 6.46 | 6.50 | 6.55 | 6.59 |

From Colt, J.: "Computation of Dissolved Gas Concentrations in Water as Functions of Temperature, Salinity, and Pressure," American Fisheries Society Special Publication 14, Bethesda, MD, 1984
Note: ppt = parts per thousand Alternatively, since ozone is a strong oxidant and disinfectant that decomposes into molecular oxygen upon storage in solution, it is the preferred source of oxygenation.

The invention also provides a method of forming a sealed, pressurized aqueous solution containing a supersaturated concentration of dissolved oxygen. The method comprises:

The container is tightly sealed so that the supersaturated oxygen cannot leak out. The container is usually made of glass or plastic, or other materials used by vendors of soft drinks, and the bottling process is similar to those for carbonated beverages. Typically, the solution is stored under a slight positive pressure of 2.0 to 6.0 atmospheres, since this increases the solubility of dissolved oxygen.

EXAMPLE

Evaluation of Clinical Effectiveness

The clinical effectiveness of oxygenated beverages in reducing halitosis as measured by a halimeter (Interscan Corporation, Chatsworth, Calif.) is illustrated by the results described in the following Table 2:

TABLE 2

| | Number of subjects | Average initial oral volatile sulfur compound concentration, as parts per billion of hydrogen sulfide in air | Average oral volatile sulfur compound concentration, as parts per billion of hydrogen sulfide in air, 5 minutes after ingesting 12 ounces of water | Average oral volatile sulfur compound concentration, as parts per billion of hydrogen sulfide in air, 30 minutes after ingesting 12 ounces of water |
|---|---|---|---|---|
| Control: Tap water chilled to 32 degrees F | 5 | 130 | 80 | 103 |
| Tap water chilled to 32 degrees F and supersaturated with pure oxygen at a gauge pressure of 50 pounds per square inch | 5 | 130 | 65 | 70 |

It is to be noted that the concentration of volatile sulfur compounds found to be offensive varies upon the olfactory sensitivity of the individual being offended. However, concentrations of approximately 100 parts per billion in air typically are offensive to most individuals at a range from the source of approximately 18 inches, especially upon exhalation by the offending party.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A method of alleviating a condition of halitosis in a person, the method comprising contacting the person's oral cavity with a aqueous solution containing a supersaturated concentration of dissolved oxygen.

2. The method of claim 1, wherein malodor in the oral cavity is reduced.

3. The method of claim 1, wherein the aqueous solution is a beverage.

4. The method of claim 1, wherein the oxygen is present at a concentration from about 20 to about 1000 mg/l.

5. The method of claim 1, the method further comprising ingesting the solution.

* * * * *